(12) United States Patent
Ranganath et al.

(10) Patent No.: US 12,326,974 B2
(45) Date of Patent: *Jun. 10, 2025

(54) INFORMATION PROCESSING SYSTEM, INFORMATION PROCESSING METHOD, AND STORAGE MEDIUM

(71) Applicant: NEC Corporation, Tokyo (JP)

(72) Inventors: Kris Ranganath, Sacramento, CA (US); Erwin Alva, Sacramento, CA (US)

(73) Assignee: NEC CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 18/637,497

(22) Filed: Apr. 17, 2024

(65) Prior Publication Data
US 2024/0264667 A1  Aug. 8, 2024

Related U.S. Application Data

(63) Continuation of application No. 17/631,013, filed as application No. PCT/JP2020/030924 on Aug. 7, 2020, now Pat. No. 11,983,312.

(Continued)

(51) Int. Cl.
*G06F 3/01* (2006.01)
*G06F 3/04817* (2022.01)
(Continued)

(52) U.S. Cl.
CPC .......... *G06F 3/013* (2013.01); *G06F 3/04817* (2013.01); *G06F 3/04847* (2013.01);
(Continued)

(58) Field of Classification Search
CPC ...... G06F 3/013; G06F 3/015; G06F 3/04817; G06F 3/04847; G06T 3/60; G06T 11/001; G06V 40/197; G06V 40/67; G06V 40/193
See application file for complete search history.

(56) References Cited

U.S. PATENT DOCUMENTS 8,340,364 B2  12/2012  Tosa ............... G06V 40/18 382/172
8,411,910 B2   4/2013  Savvides ......... G06V 40/18 382/117

(Continued)

FOREIGN PATENT DOCUMENTS

EP    1767174 A2    3/2007
JP    2000-066800 A 3/2000

(Continued)

OTHER PUBLICATIONS

International Search Report for PCT Application No. PCT/JP2020/030924, mailed on Oct. 20, 2020.

(Continued)

*Primary Examiner* — Antonio A Caschera

(57) ABSTRACT

An information processing apparatus includes: a memory configured to store one or more instructions; and a processor configured to execute the one or more instructions to: obtain a first image including a first representation of an iris region of a first eye; obtain a second image including a second representation of an iris region of a second eye; receive an input to rotate at least one of the first image or the second image; and control a display to display the at least one of the first image or the second image in a rotated state based on the input.

15 Claims, 13 Drawing Sheets

Related U.S. Application Data

(60) Provisional application No. 62/884,833, filed on Aug. 9, 2019.

(51) Int. Cl.
  *G06F 3/04847* (2022.01)
  *G06T 3/60* (2006.01)
  *G06T 11/00* (2006.01)
  *G06V 10/143* (2022.01)
  *G06V 10/50* (2022.01)
  *G06V 40/18* (2022.01)
  *G06V 40/60* (2022.01)

(52) U.S. Cl.
  CPC .............. *G06T 3/60* (2013.01); *G06T 11/001* (2013.01); *G06V 10/143* (2022.01); *G06V 10/50* (2022.01); *G06V 40/193* (2022.01); *G06V 40/197* (2022.01); *G06V 40/67* (2022.01)

(56) References Cited

U.S. PATENT DOCUMENTS

| | | | |
|---|---|---|---|
| 11,983,312 B2 * | 5/2024 | Ranganath | G06T 11/001 |
| 2003/0151720 A1 | 8/2003 | Chernyak et al. | |
| 2007/0055222 A1 | 3/2007 | Hohla et al. | |
| 2007/0146633 A1 | 6/2007 | LeBlanc et al. | |
| 2007/0201728 A1 | 8/2007 | Monro | |
| 2010/0074477 A1 | 3/2010 | Fujii et al. | |
| 2020/0082587 A1 | 3/2020 | Inoue | |

FOREIGN PATENT DOCUMENTS

| | | |
|---|---|---|
| JP | 2008-090482 A | 4/2008 |
| JP | 2015-513747 A | 5/2015 |
| KR | 10-2016-0138805 A | 12/2016 |
| WO | 2007/096657 A3 | 8/2007 |
| WO | 2019/106912 A1 | 6/2019 |

OTHER PUBLICATIONS

Extended European Search Report for EP Application No. 20853305.9, dated on Jul. 27, 2022.

JP Office Action for JP Application No. 2022-534885, mailed on Jul. 11, 2023 with English Translation.

English machine translation of Ayatsuka, JP2000-066800 via Espacenet (Year: 2000).

EP Office Action for EP Application No. 20853305.9, mailed on Jul. 22, 2024.

* cited by examiner

INFORMATION PROCESSING SYSTEM, INFORMATION PROCESSING METHOD, AND STORAGE MEDIUM

This application is a continuation application of U.S. patent application Ser. No. 17/631,013 filed on Jan. 28, 2022, which is a National Stage Entry of PCT/JP2020/030924 filed on Aug. 7, 2020, which claims priority from U.S. Provisional Patent Application 62/884,833 filed on Aug. 9, 2019, the contents of all of which are incorporated herein by reference, in their entirety.

TECHNICAL FIELD

The disclosure relates to an information processing system, an information processing method, and a storage medium, more particularly, to an information processing system, an information processing method, and a storage medium for performing an authentication using an iris image.

BACKGROUND ART

Patent Literature 1 (Japanese Patent Application Publication No. 2008-90482) discloses an authentication system for authenticating an individual by encoding a feature of an iris image. This authentication system performs the authentication by comparing a code of an iris image of the individual registered in advance with a code of an iris image acquired at the time of authentication, and displaying a notification window with an authentication result on a display unit of the authentication system.

SUMMARY

While the authentication system of Patent Literature 1 discloses outputting the result of the authentication (i.e. whether the individual is authenticated or not), Patent Literature 1 does not disclose providing the user with information regarding the iris comparison in addition to the result of the authentication. However, it may be desirable to provide a user interface to assist the user to better understand details of the iris comparison and the result of the authentication.

One or more example embodiments of the disclosure may address the above problems and may provide an information processing system, an information processing method, and a storage medium with an improved graphical user interface that can display information regarding iris comparison in association with positions in an iris.

According to an aspect of the disclosure, there is provided an information processing apparatus comprising: a memory configured to store one or more instructions; and a processor configured to execute the one or more instructions to: obtain a first image including a first representation of an iris region of a first eye; obtain a second image including a second representation of an iris region of a second eye; receive an input to rotate at least one of the first image or the second image; and control a display to display the at least one of the first image or the second image in a rotated state based on the input.

The first representation may be based on a first feature amount calculated for the iris region of the first eye in the first image, and the second representation may be based on a second feature amount calculated for the iris region of the second eye in the second image.

The first representation and the second representation may be based on a result of comparison between the iris region of the first eye in the first image and the iris region of the second eye in the second image.

The first representation and the second representation may comprise an indication of a matching region, a non-matching region, or a non-comparable region based on the results of the comparison.

The matching region, the non-matching region, or the non-comparable region may be indicated by coloring the iris region of the first eye in the first image or the iris region of the second eye in the second image in a predetermined color.

The processor may be further configured to generate the first feature amount and the second feature amount by dividing the iris region of the first eye in the first image and the iris region of the second eye in the second image into a plurality of blocks associated with the positions in the iris of the respective eye, and setting a code extracted from the iris image for each of the plurality of blocks.

The first representation may be based on a coded image corresponding to the iris region of the first eye in the first image, and the second representation may be based on coded image corresponding to the iris region of the second eye in the second image.

The processor may be further configured to simultaneously display the first image and the second image.

The processor may be further configured to display a dial icon for guiding a user to input an instruction to rotate the first image and the second image.

The processor may be further configured to display a dial icon for guiding a user to input an instruction to align the first image with the second image.

The first image may be a photograph of an eye of a recognition subject, and the second image may be a registered image, among a plurality of registered images stored in a storage.

According to another aspect of the disclosure, there is provided an information processing method comprising: obtaining a first image including a first representation of an iris region of a first eye; obtaining a second image including a second representation of an iris region of a second eye; receiving an input to rotate at least one of the first image or the second image; and controlling a display to display the at least one of the first image or the second image in a rotated state based on the input.

The first representation may be based on a first feature amount calculated for the iris region of the first eye in the first image, and the second representation may be based on a second feature amount calculated for the iris region of the second eye in the second image.

The first representation and the second representation may be based on a result of comparison between the iris region of the first eye in the first image and the iris region of the second eye in the second image.

The first representation and the second representation may comprise an indication of a matching region, a non-matching region, or a non-comparable region based on the results of the comparison.

The matching region, the non-matching region, or the non-comparable region may be indicated by coloring the iris region of the first eye in the first image or the iris region of the second eye in the second image in a predetermined color.

The information processing method may further comprise generating the first feature amount and the second feature amount by dividing the iris region of the first eye in the first image and the iris region of the second eye in the second image into a plurality of blocks associated with the positions in the iris of the respective eye, and setting a code extracted from the iris image for each of the plurality of blocks.

The first representation may be based on a coded image corresponding to the iris region of the first eye in the first image, and the second representation may be based on coded image corresponding to the iris region of the first eye in the second image.

The information processing method may further comprise displaying a dial icon for guiding a user to input an instruction to rotate the first image and the second image.

According to another aspect of the disclosure, there is provided a non-transitory computer readable medium having stored thereon a program for performing a method comprising: obtaining a first image including a first representation of an iris region of a first eye; obtaining a second image including a second representation of an iris region of a second eye; receiving an input to rotate at least one of the first image or the second image; and controlling a display to display the at least one of the first image or the second image in a rotated state based on the input.

DESCRIPTION OF EXAMPLE EMBODIMENTS

One or more example embodiments of the disclosure will be described below with reference to the drawings. Throughout the drawings, the same components or corresponding components are labeled with the same references, and the description thereof may be omitted or simplified.

Figure 1:
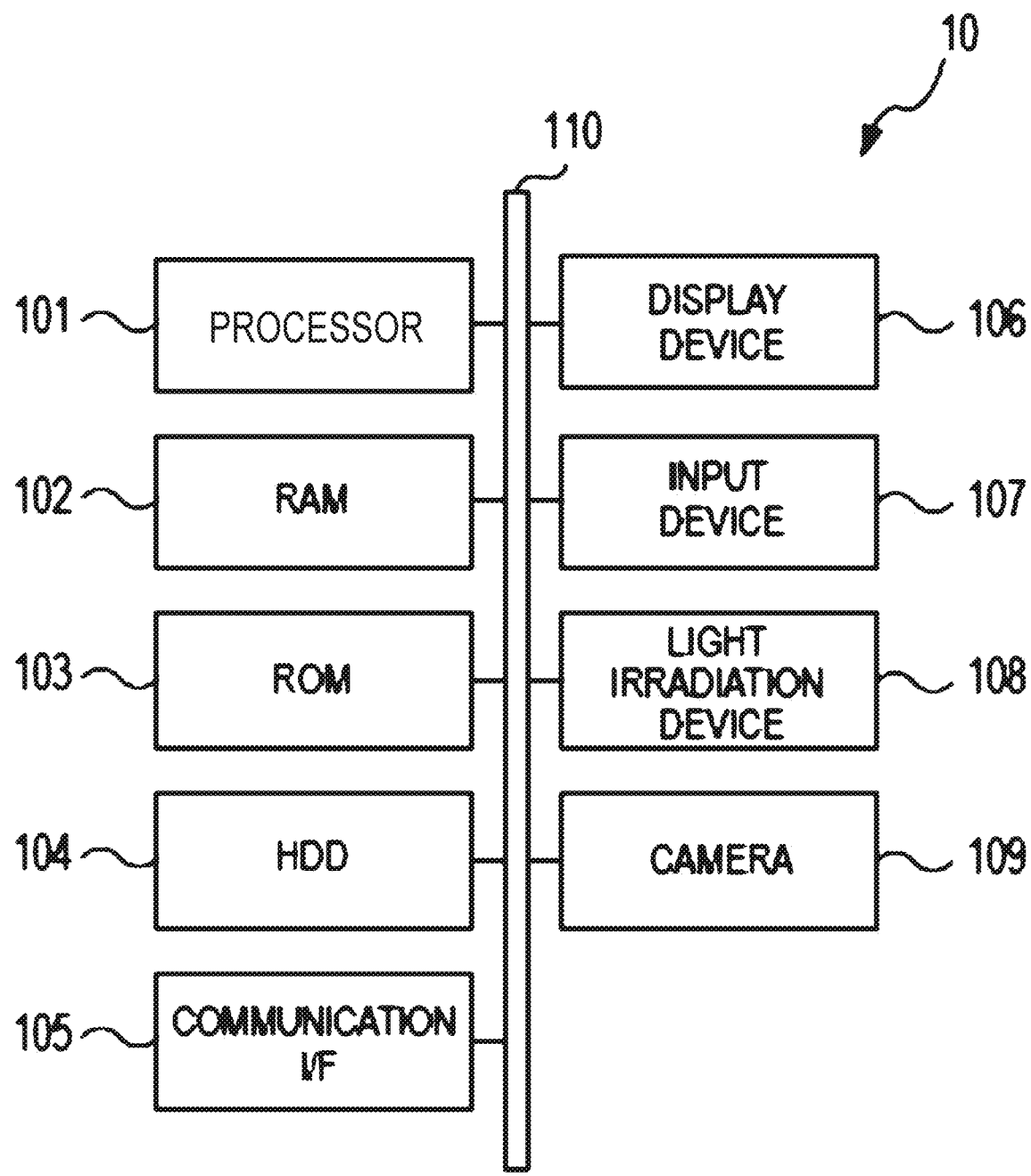
FIG. 1 is a block diagram illustrating a hardware configuration of an information processing system according to an example embodiment.

FIG. 1 is a block diagram illustrating a hardware configuration of an information processing system 10 according to an example embodiment. The information processing system 10 may be, for example, an iris recognition apparatus. Further, the information processing system 10 has a function of a computer. For example, the information processing system 10 may be configured integrally with a desktop personal computer (PC), a laptop PC, a tablet PC, a smartphone, or the like. The information processing system 10 has a function of iris comparison, which is a type of biometrics recognition. The information processing system 10 captures an image (an iris image) including an iris of a recognition subject and performs iris comparison by comparing the captured image with a registered iris image. The pattern of an iris that adjusts the opening diameter of a pupil is unique and permanent for a person. It is therefore possible to perform identity verification by comparing a pattern of an iris acquired at the time of comparison with an iris image registered in advance.

The information processing system 10 may be applied to, for example, identity verification at the time of login into a PC, identity verification for entry into or departure from a country at an airport, a seaport, or a boundary, identity verification in a government office, identity verification for entry into or exit from a factory or an office, identity verification at the time of entry into an event site, or the like.

The information processing system 10 has a processor 101, a random access memory (RAM) 102, a read only memory (ROM) 103, and a hard disk drive (HDD) 104 in order to implement functions as a computer that performs operation and storage. Further, the information processing system 10 has a communication interface (I/F) 105, a display device 106, an input device 107, a light irradiation device 108, and a camera 109. The processor 101, the RAM 102, the ROM 103, the HDD 104, the communication I/F 105, the display device 106, the input device 107, the light irradiation device 108, and the camera 109 are connected to each other via a bus 110. According to an example embodiment, the display device 106, the input device 107, the light irradiation device 108, and the camera 109 may be connected to the bus 110 via a drive device (not illustrated) used for driving these devices. According to an example embodiment, the processor 101 may be a central processing unit (CPU), a controller, or the like. According to another example embodiment, the processor may be a hardware processor. According to another example embodiment, the processor may be implemented by a combination of hardware and software components. According to another example embodiment, the processor may be implemented by a configuration of electronic components including one or more circuitry components.

While respective components forming the information processing system 10 are illustrated in FIG. 1 as an integrated device, some of the components and/or some of the functions performed by the components thereof may be by an externally attached device. For example, the display device 106, the input device 107, the light irradiation device 108, and the camera 109 may be externally attached devices that are separate from a part performing the function of a computer including the processor 101 or the like. At this time, the light irradiation device 108 and the camera 109 may be a part of an externally attached iris recognition apparatus of the information processing system 10. In such a case, the information processing system 10 may be an information display apparatus for displaying information acquired by the iris recognition apparatus.

The processor 101 has a function of performing an operation in accordance with a program stored in the ROM 103, the HDD 104, or the like and controlling each component of the information processing system 10. According to an example embodiment, the processor 101 may obtain one or more instructions stored in the ROM 103, the HDD 104, or the like and execute the one or more instructions to perform one or more operations. The one or more operations may include controlling one or more components of the information processing system 10 to perform one or more operations. The RAM 102 is formed of a volatile storage medium and provides a temporary memory field required for the operation of the processor 101. The ROM 103 is formed of a nonvolatile storage medium and stores necessary information such as a program used in the operation of the information processing system 10. The HDD 104 is a storage device that is formed of a nonvolatile storage medium and stores an image captured by the camera 109 or the like, an image of a recognition subject, a feature amount, or the like.

The communication I/F 105 is a communication interface based on a specification such as Wi-Fi (registered trademark), 4G, or the like, which is a module for communicating with other devices. The display device 106 is a liquid crystal display, an organic light emitting diode (OLED) display, or the like and is used for displaying a moving image, a static image, a text, or the like. The input device 107 is a button, a touchscreen, a keyboard, a pointing device, or the like and is used by a user to operate the information processing system 10. The display device 106 and the input device 107 may be integrally formed as a touchscreen.

The light irradiation device 108 may provide a light source for the camera 109 to capture an image. The camera 109 can capture an eye of a recognition subject or the like by using a light emitted from the light irradiation device 108 and acquire an image. A digital camera using a Complementary Metal Oxide Semiconductor (CMOS) image sensor, a Charge Coupled Device (CCD) image sensor, or the like may be used as the camera 109 so as to be suitable for image processing after capturing.

According to an example embodiment, a light emitted from the light irradiation device 108 is not limited to a visible light and may be an infrared light. In such a case, the light irradiation device 108 may include a light emitting element such as an infrared LED that emits an infrared light. Furthermore, the camera 109 may include a light receiving element configured to have a sensitivity to infrared rays. The light irradiation device 108 irradiates an eye of a recognition subject with an infrared light and captures an infrared ray reflected by an iris by using the camera 109, and thereby an iris image used in iris comparison can be captured. By acquiring an iris image by using an infrared ray, it is possible to obtain a high contrast image regardless of the color of the iris and reduce an influence of a reflection by a cornea. According to an example embodiment, the wavelength of an infrared ray irradiated from the light irradiation device 108 may be, for example, a near-infrared region around 800 nm. When the above influence of a reflection by a cornea is not a problem, however, the light irradiation device 108 and the camera 109 may be devices for a visible light.

According to an example embodiment, the hardware configuration illustrated in FIG. 1 is an example, and a device other than the devices thereof may be added, or some of the devices may not be provided. Further, some of the devices may be replaced with another device having a similar function. Furthermore, some of the functions may be provided by another device via a network, or the functions forming the example embodiment may be implemented by being distributed in a plurality of devices. For example, the HDD 104 may be replaced with a solid state drive (SSD) using a semiconductor element such as a flash memory or may be replaced with cloud storage.

Figure 2:
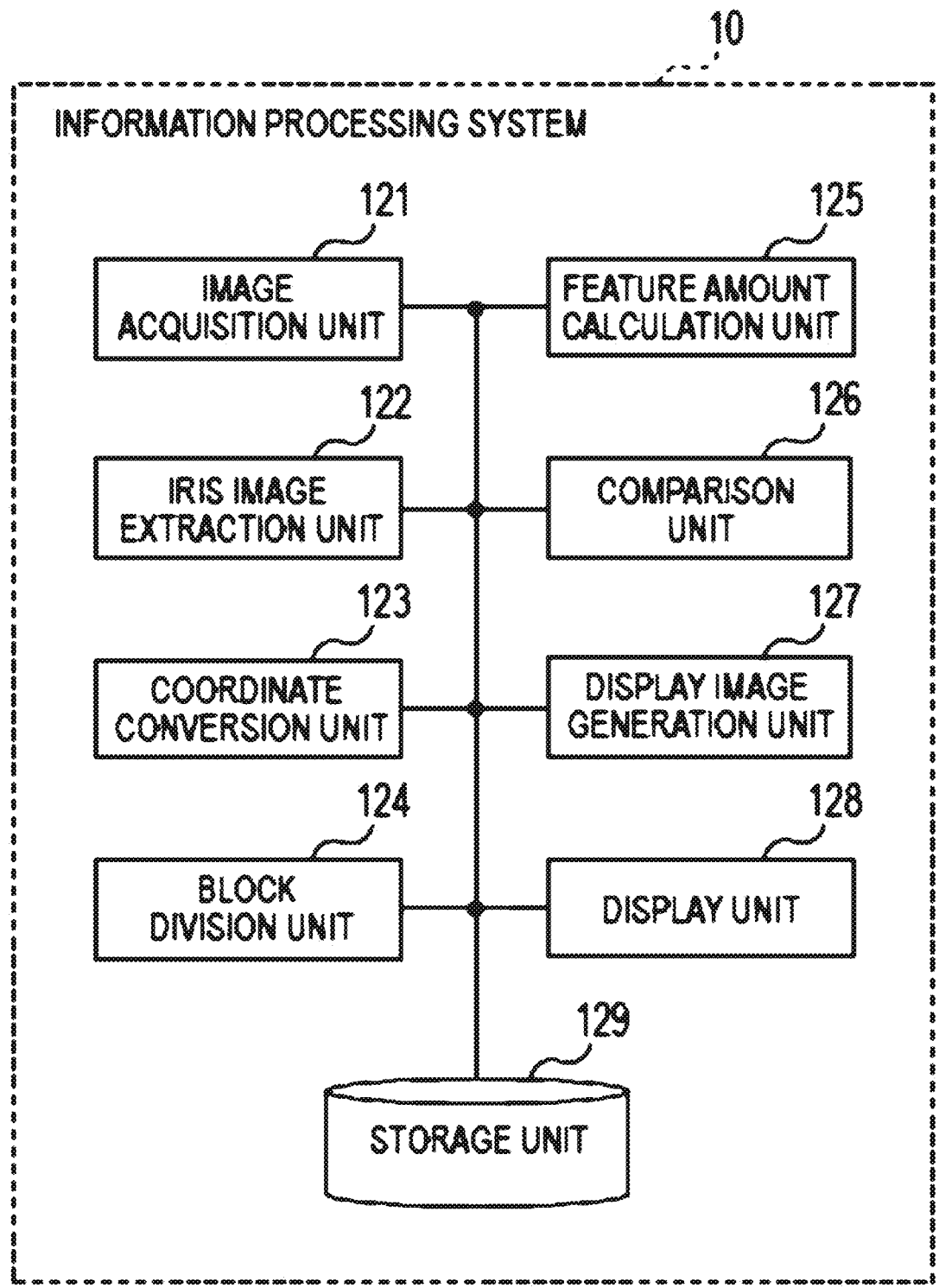
FIG. 2 is a function block diagram of the information processing system according to the example embodiment.

FIG. 2 is a function block diagram of the information processing system 10 according to an example embodiment. The information processing system 10 has an image acquisition unit 121, an iris image extraction unit 122, a coordinate conversion unit 123, a block division unit 124, a feature amount calculation unit 125, a comparison unit 126, a display image generation unit 127, a display unit 128, and a storage unit 129.

The processor 101 implements the function of the image acquisition unit 121 that acquires an image of an eye of a recognition subject by controlling the light irradiation device 108 and the camera 109. The processor 101 loads and executes a program stored in the ROM 103 or the like to the RAM 102 and thereby implements the functions of the iris image extraction unit 122, the coordinate conversion unit 123, the block division unit 124, the feature amount calculation unit 125, the comparison unit 126, and the display image generation unit 127. The process performed by each of these units will be described later. The display unit 128 displays a display image generated by the display image generation unit 127. The processor 101 implements the function of the display unit 128 by controlling the display device 106. The storage unit 129 stores data such as an image of an eye acquired by the image acquisition unit 121, an image of an eye registered in advance, an iris image extracted therefrom, a feature amount calculated from the iris image, or the like. The processor 101 implements a function of the storage unit 129 by controlling the HDD 104.

Figure 3:
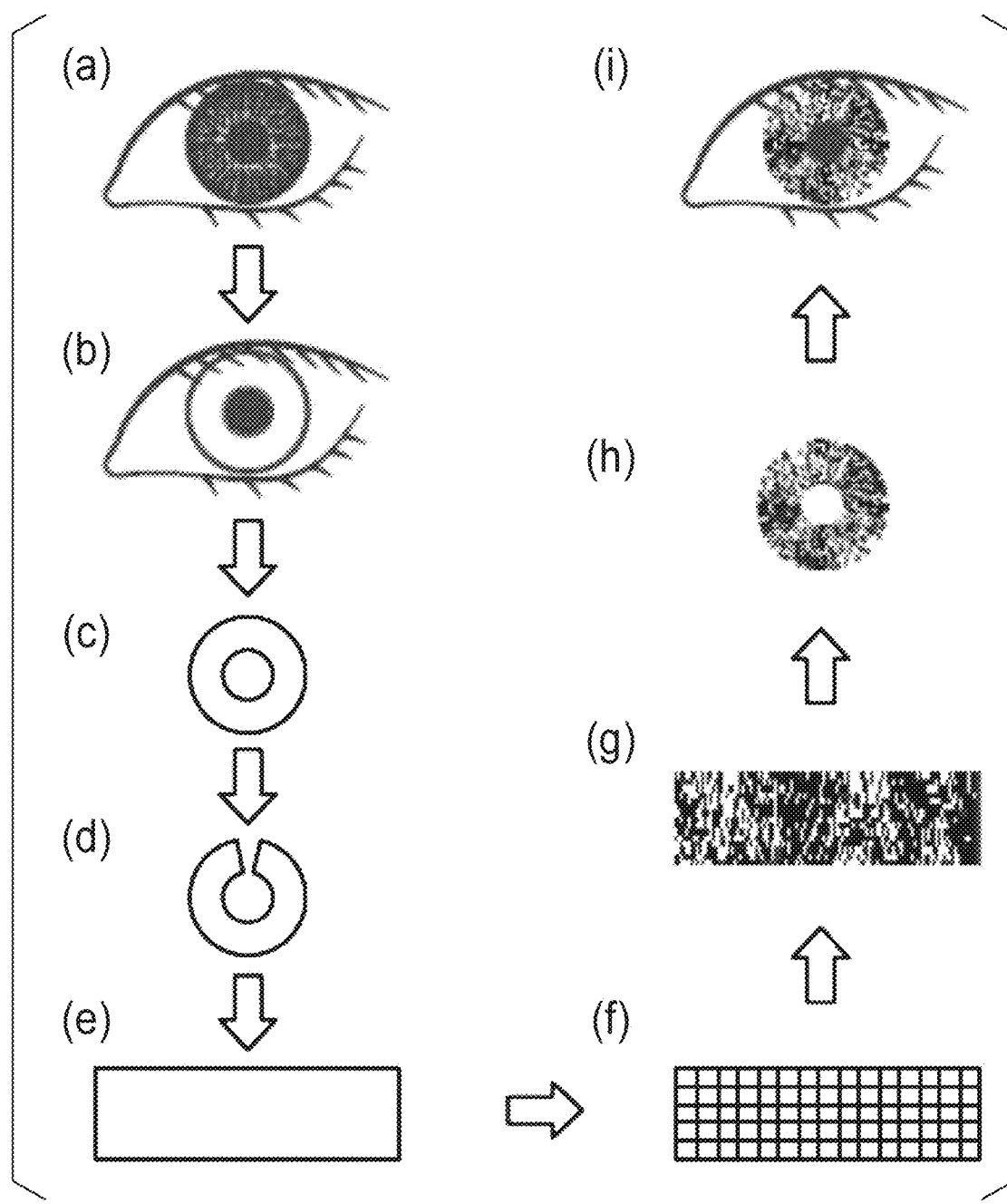
FIG. 3 is a schematic diagram illustrating the outline of a process performed by the information processing system according to the example embodiment.
Figure 4:
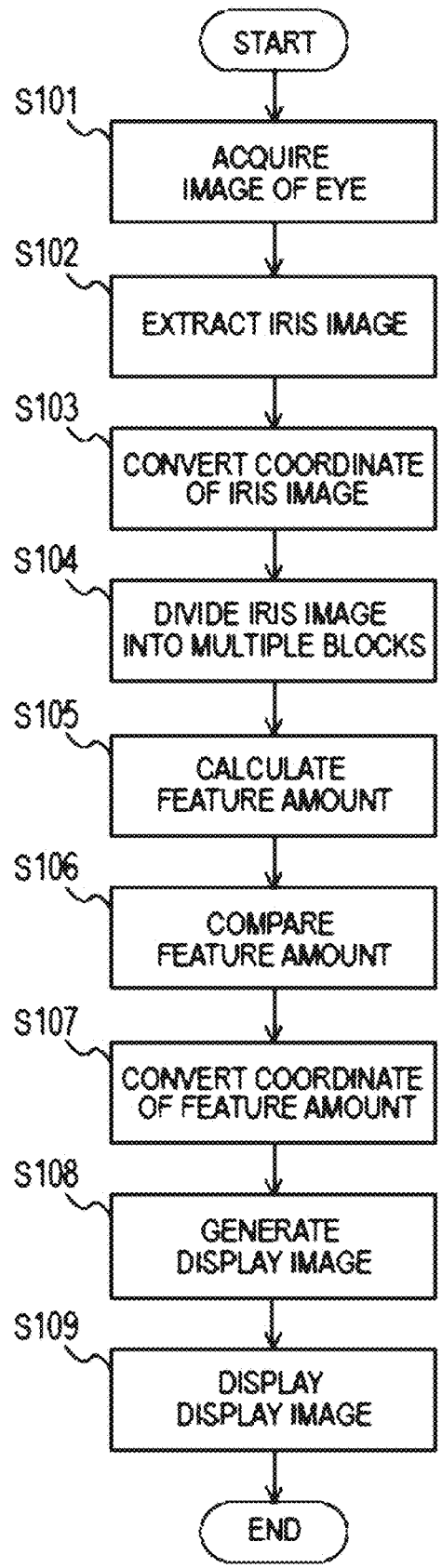
FIG. 4 is a flowchart illustrating the outline of a process performed by the information processing system according to the example embodiment.

FIG. 3 is a schematic diagram illustrating the outline of the process performed by the information processing system 10 according to an example embodiment. FIG. 4 is a flowchart illustrating the outline of the process performed by the information processing system 10 according to an example embodiment. With reference to FIG. 3 if necessary, the outline of the process performed by the information processing system 10 will be described along the flowchart of FIG. 4.

In S101 of FIG. 4, the image acquisition unit 121 acquires an image of an eye of a recognition subject. This process corresponds to Portion (a) of FIG. 3. The acquired image is stored in the storage unit 129. Typically, this image is acquired by using an infrared ray, which is a grayscale image.

In S102 of FIG. 4, the iris image extraction unit 122 determines a region of an iris from the image of the eye of the recognition subject and extracts an iris image. This process corresponds to Portion (b) of FIG. 3 and Portion (c) of FIG. 3.

According to an example embodiment, the method of determining a region of an iris may include the following operations performed by the iris image extraction unit 122. For example, the iris image extraction unit 122 detects a pupil from an image of an eye and determines the position thereof. The determined pupil position is stored in the storage unit 129. The shape of a pupil can be approximated as a circle. Thus, a position of a pupil can be expressed by the center coordinates and the radius of the pupil, for example. Note that a region of a pupil can be detected by extracting a pixel having brightness lower than a predetermined value, for example.

The iris image extraction unit 122 then detects an iris from the image of the eye and determines the position of the iris. The determined position of the iris is stored in the storage unit 129. A shape of an iris can be approximated as a ring shape including a pupil, and thus a position of an iris can be expressed by the center coordinates, the outer circumference radius, and the inner circumference radius of the iris, for example. The inner circumference radius of an iris corresponds to the radius of a pupil and thus may be omitted from information indicating the position of the iris. Note that an iris can be detected by extracting brightness change on the boundary between the outer circumference of the iris and a sclera (a so-called white of eye), for example.

The iris image extraction unit 122 then extracts an iris image by cutting out a portion of the determined iris. The extracted iris image is stored in the storage unit 129.

In S103, the coordinate conversion unit 123 transforms the iris image by performing coordinate conversion. This process corresponds to Portion (d) of FIG. 3 and Portion (e) of FIG. 3. As illustrated in Portion (d) of FIG. 3 and Portion (e) of FIG. 3, the coordinate conversion unit 123 converts a ring-shaped iris image into a rectangle. This process may be performed by converting the coordinate system of an iris image from an x-y plane coordinate system into an r-q polar coordinate system, for example. Since such coordinate conversion simplifies the shape of an iris image, the process of feature amount calculation is simplified.

In S104, the block division unit 124 divides the iris image converted to a rectangle into a plurality of blocks. This process corresponds to Portion (f) of FIG. 3. The number of divisions may be, for example, 128 in the horizontal direction and 16 in the vertical direction (that is, 2048 in total) or the like. Note that, while Portion (f) of FIG. 3 expresses the iris image itself as being cut and divided into a plurality of pieces for easier understanding, it is not essential to divide an image into a plurality of pieces. The process of step S104 may be a process to acquire a correspondence between the brightness of each block of an iris image and the coordinates of each block, for example.

In S105, the feature amount calculation unit 125 performs a process to calculate feature amounts on the iris image divided into a plurality of blocks. This process corresponds to Portion (g) of FIG. 3. An example of a specific processing method of feature amount calculation will be described below.

The feature amount calculation unit 125 acquires the brightness in each block of the iris image. At this time, a feature amount code of a certain block (hereafter, referred to as a first block) is set in accordance with a level relationship of brightness relative to a block which is right next to the first block (hereafter, referred to as a second block). When the difference resulted by subtracting the brightness of the second block from the brightness of the first block is larger than a first threshold, the feature amount code of the first block is "1". When the difference resulted by subtracting the brightness of the second block from the brightness of the first block is less than or equal to the first threshold and greater than a second threshold, the feature amount code of the first block is "2". When the difference resulted by subtracting the brightness of the second block from the brightness of the first block is less than or equal to the second threshold, the feature amount code of the first block is "3". In such a way, the feature amount code has at least three types of values. Note that, while three types of feature amount codes are set by using two types of thresholds in the example described above, the number of the types of thresholds is an example and may be suitably set. For example, when one type of threshold is used (only the first threshold), the feature amount code may be two types of "1" or "2". Further, when three or more types of thresholds are used, the feature amount code will be four or more types such as "1", "2", "3", "4", . . . . As discussed above, the number of types of the feature amount code may be any number of two or more in accordance with the number of types of thresholds.

Further, when the first block or the second block is covered with eyelashes, an eyelid, or the like and unable to be used for feature amount calculation, a code other than a feature amount code set in accordance with the level relationship of brightness may be set.

As one example, when a feature amount code set in accordance with the level relationship of brightness has three types of "1", "2", and "3", a feature amount code indicating that no feature amount can be calculated may be "4". In such a case, the feature amount code has four types of values. In the following description, the feature amount code has the four types described above.

Portion (g) of FIG. 3 illustrates a feature amount image in which feature amount codes are depicted at respective block positions. In the feature amount image of Portion (g) of FIG. 3, values "1", "2", "3", and "4" of the feature amount code are displayed by different patterns. This display may be display in which the image pattern such as the color, the brightness, the pattern, or the like may be changed in accordance with the value of the code, for example. The extracted feature amount or the extracted feature amount image is stored in the storage unit 129.

Note that, while a positional relationship in which the second block is right next to the first block is illustrated in the example described above, the second block may be left next to the first block, or more generally, it may be a positional relationship in which the second block is adjacent to the first block.

In S106, the comparison unit 126 performs a process to compare a feature amount calculated in S105 with a feature amount registered in advance. In this process, the feature amount calculated in S105 is compared with a feature amount registered in advance to determine a region where there is a matching (a matching region), a region where there is no matching (a non-matching region), and a region where no comparison can be made (a non-comparable region). For example, a region in which all the codes to be compared are "1" or "3" may be determined as a matching region. A region in which one of the codes to be compared is "1" and the other is "3" may be determined as a non-matching region. A region in which any of the codes to be compared is "4" cannot be used for comparison and thus may be determined as a non-comparable region. When a score of a matching degree calculated from the size or the like of matching regions and non-matching regions exceeds a predetermined threshold, two iris images corresponding to two feature amounts to be compared are determined to be from the same person. A comparison result and information on a matching region, a non-matching region, and a non-comparable region are stored in the storage unit 129. Note that information on a feature amount, a matching region, a nonmatching region, and a non-comparable region may be more generally referred to as comparison information regarding iris comparison.

In S107, the coordinate conversion unit 123 transforms the feature amount image by converting coordinates. This process corresponds to Portion (h) of FIG. 3. The coordinate conversion unit 123 converts a rectangular feature amount image into a ring shape. This process may be performed by converting the coordinate system of a feature amount image from an r-q polar coordinate system into an x-y plane coordinate system, for example. Such coordinate conversion provides a feature amount image in which images each indicating a value of a code of each block are arranged in a ring shape so as to correspond to the position in the iris from which each code has been generated. The converted feature amount image is stored in the storage unit 129.

In S108, the display image generation unit 127 generates a display image including one in which the feature amount image converted in the ring shape is superimposed on the image of the eye of the comparison subject acquired by S101. This process corresponds to Portion (i) of FIG. 3. The generated display image is stored in the storage unit 129. Note that an image of an eye may be a photograph of an eye of a recognition subject acquired for iris authentication as illustrated in Portion (i) of FIG. 3 but not limited thereto and may be an image of other's eye or a drawing of an eye, for example.

In S109, the display unit 128 reads a display image from the storage unit 129 and displays the display image. In the following, a display image displayed on the display unit 128 will be described in more detail.

Figure 5:
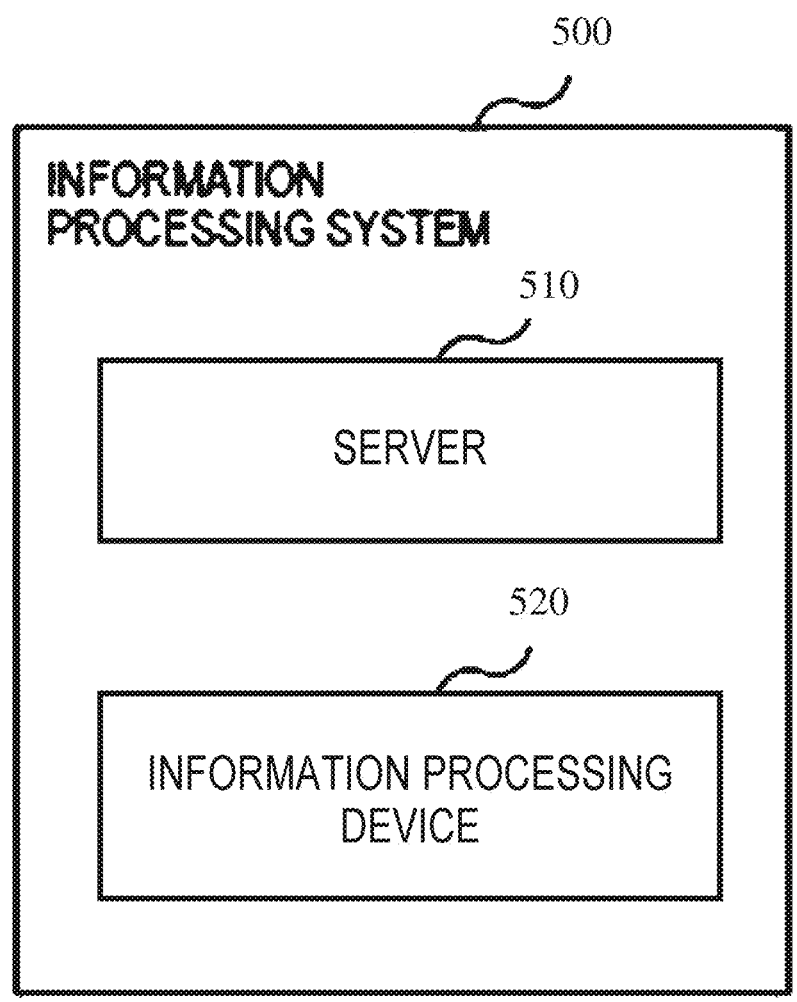
FIG. 5 illustrates an example of a display image due to the information processing system according to the example embodiment.

FIG. 5 is a function block diagram of an information processing system 500 according to an example embodiment of the disclosure. The information processing system 500 has a server 510 and an information processing device 520. The server 510 acquires comparison information regarding iris comparison generated based on an iris image including an iris of a recognition subject. The information processing device 520 generates a display image used for displaying comparison information image indicating a content of the comparison information on a display device in association with positions in the iris.

Figure 6A:
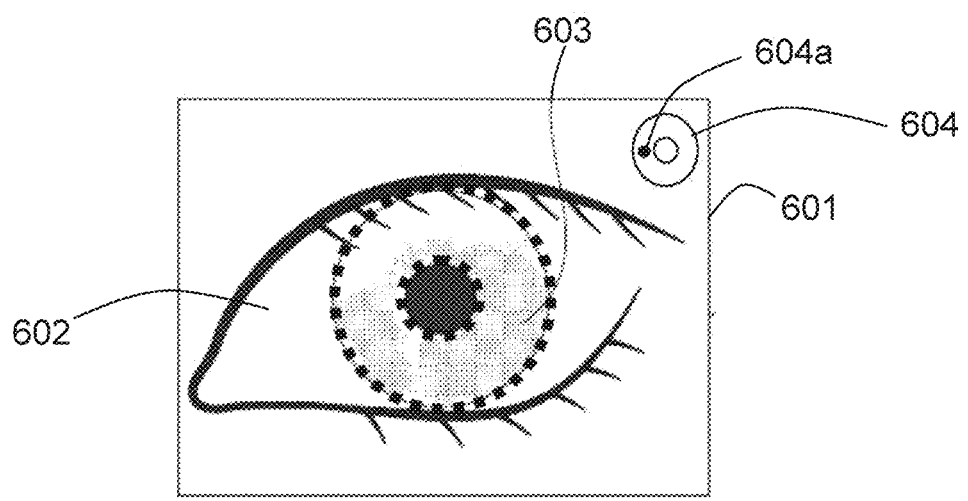
FIGS. 6A and 6B illustrate examples of display images displayed by the information processing system according to an example embodiment.
Figure 6B:
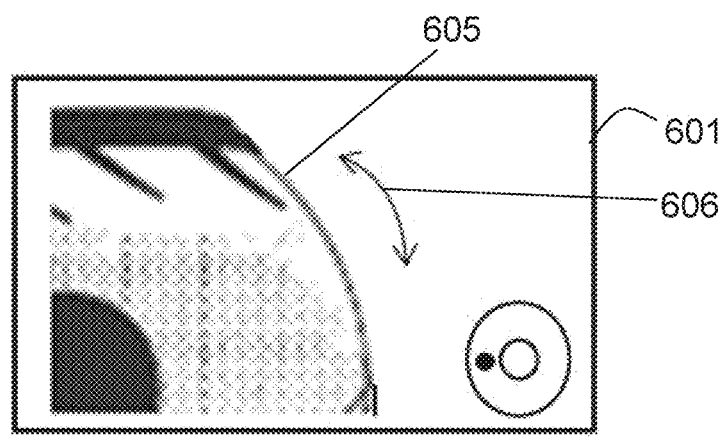

FIGS. 6A and 6B illustrate examples of a display image displayed on the display unit 128. In FIG. 6A, the display region 601 includes an image of an eye 602. According to an example embodiment, one or more pieces of information 603 related to the iris of the eye 602 may be included in the image of the eye 602. According to an example embodiment, the one or more pieces of information may be superimposed or layered on top of at least a part of the iris portion of the image. According to another example embodiment, the one or more pieces of information may replace at least part in the iris portion of the image or the one or more pieces of information may replace the entire iris portion of the image.

According to an example embodiment, the one or more pieces of information related to the iris portions of the eye may be feature amounts (i.e., calculated in operation S105 in FIG. 4), iris code of the eye, representations of a result of a comparison (i.e., an indication of a matching region, an indication of a non-matching region or an indication of a region unable to be compared determined in operation S105).

According to the example embodiment, the display screen 601 includes a dial 604 having a pointer 604a representing a position of rotation of the iris portion. For example, as the user rotates the iris image around a central axis of the pupil of the eye, the pointer 604a moves around the dial in a corresponding manner. In this manner, the user is able to easily align images of the eye. According to an example embodiment, an entire portion of the eye may be rotated. According to an example embodiment, only a portion of the eye may be rotated. For instance, according to an example embodiment, only the ring shaped iris portion may be rotated. According to an example embodiment, the user may use a mouse cursor, touch or a dial input interface (such as Microsoft Surface Dial).

FIG. 6B illustrates an example embodiment in which a portion of the eye is displayed in the display region 601. In FIG. 6B, only a quarter portion of the iris image 605 is displayed with a center of the pupil being a center rotation. In this manner, the user is able to view the details of the iris image more closely. For instance, based on the user input for rotation, the portion of the iris image rotates around the central axis formed at the center of the pupil. The input for rotation may be a clockwise direction or a counter-clockwise direction as depicted by arrow 606. In this manner, the user may be able to closely verify the entire iris image section by section by rotating the iris image.

Figure 6C:
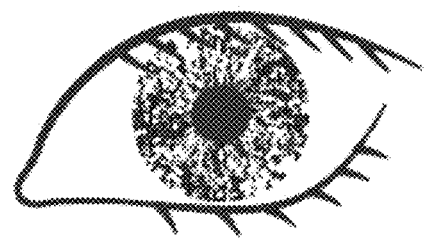
FIG. 6C illustrates an example of a coded image according to an example embodiment.

FIG. 6C illustrates an example of a coded image according to an example embodiment. According to an example embodiment, a representation of the coded image may be depicted with specific shades of black and white regions. According to an example embodiment, the shades of black and white regions may be determined based on a comparison of a brightness value of each block with a brightness value of a block adjacent to each of the respective block.

FIG. 7 is an example of a display image displayed on the display unit 128 for verification. In the displayed image, a display region 701 provided with a caption of "Probe Image" and a display region 702 provided with a caption of "Gallery Image" are displayed so as to be arranged side by side. According to an example embodiment, the display regions 701 and 702 are arranged in a horizontal direction. According to another example embodiment, the display regions 701 and 702 may be arranged in a vertical direction. According to an example embodiment, the display region 701 is a region that displays a first image of an eye acquired as a candidate for comparison with a second image of an eye. According to an example embodiment, the image generated in operation S108 may be the first image of the eye, i.e., "Probe Image", displayed in the display region 701. According to an example embodiment, the display region 702 is a region that displays the second image of the eye. According to an example embodiment, the second image of the eye may be an image obtained from a storage storing a plurality of preregistered images each corresponding to an eye. According to another example embodiment, multiple first images or the second images may be simultaneously displayed on a display screen 700.

The first image displayed in the display region 701 and the second image displayed in the display region 702 may be one obtained by scaling up or scaling down an image actually captured. Thereby, an image of an eye acquired at comparison and an image of an eye acquired at registration can be displayed as of the same size even when the original sizes thereof are different from each other. At this time, by setting the magnification of scale up or scale down so as to have substantially the same size of irises, the visual sizes of the images of the eyes can be closer.

According to an example embodiment, the user of the information processing system 10 can check a reliability of the iris comparison by verifying a degree of match between the first image ("Probe Image") and the second image ("Gallery Image"). For example, the information processing system 10 provides a graphical user interface (GUI) that allows a user to rotate an iris image in order to closely observe the iris image.

According to an example embodiment, one or more pieces of information corresponding to the first image of the eye acquired at comparison (i.e., "Probe Image") may be arranged vertically and displayed in the left in the display image, and one or more pieces of information corresponding to the second image of the eye registered in advance (i.e., "Gallery Image") may be arranged vertically and displayed in the right in the display image. According to an example embodiment, the one or more pieces of information may be superimposed on the iris portion of the eye in the first image, the second image or both the first image and the second image. Thus, the user of the information processing system 10 can understand information regarding iris comparison at a glance.

According to an example embodiment, the display screen 700 may provide a plurality of selectable icons 703, which the user may select to perform various functions. For example, the user may select one of the icons 703 to select the one or more pieces of information to add to the image of the iris. According to another example, the icon buttons 703 may be used for selecting a zoom operation. According to another embodiment, the various functions may be selected through a selectable drop down menu, selectable buttons, selectable fields, voice commands or any other type of interactive menu selection methods available for a graphical user interface.

Figure 7A:
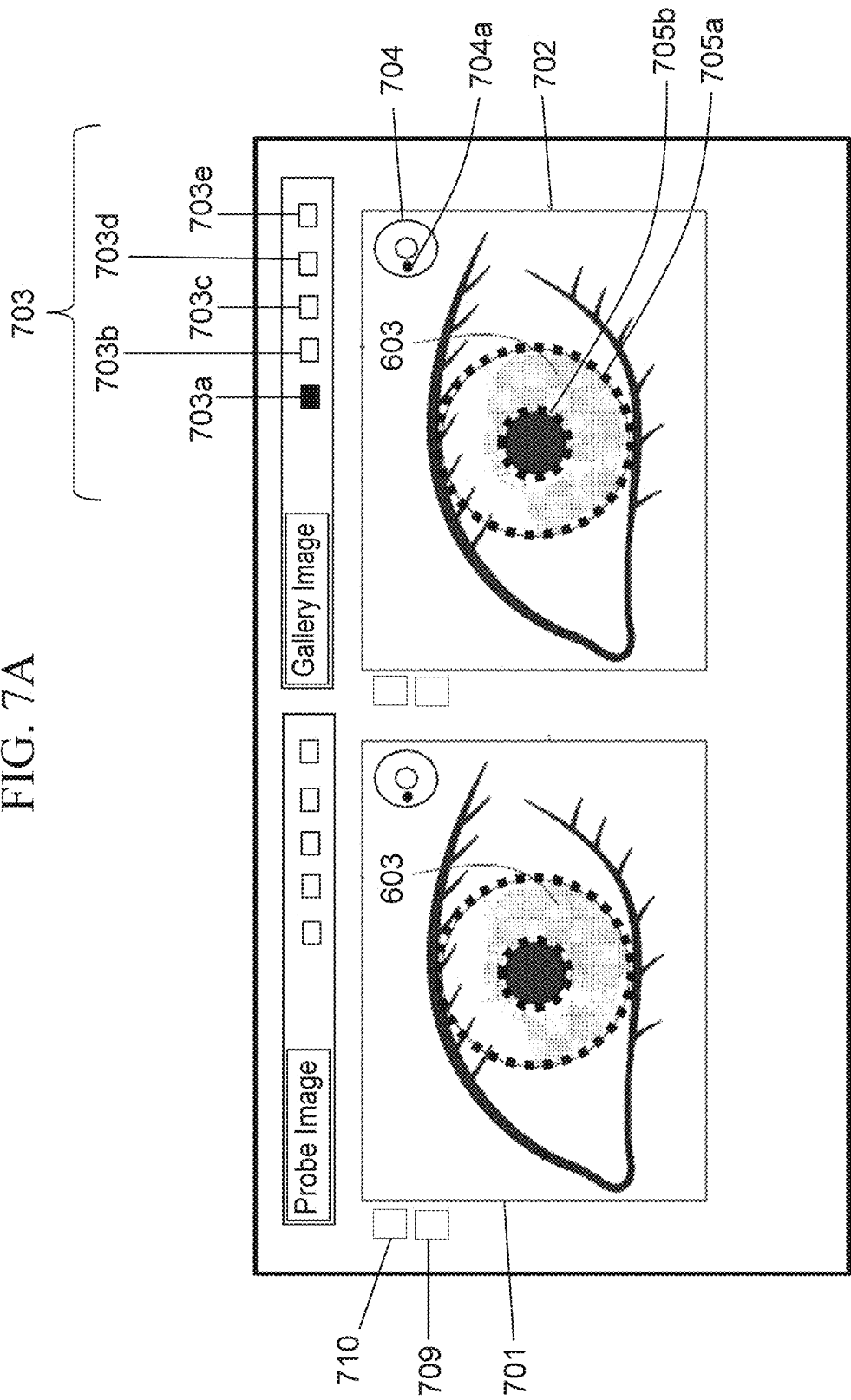
FIGS. 7A-7D illustrate an example of a display screen displayed by the information processing system according to an example embodiment.

According to an example embodiment illustrated in FIG. 7A, a border function may be provided that draws a border around the iris of the eye. For instance, when icon 703a is selected, the processor 101 identifies a boundary of the iris and generates a border to be provided on the displayed iris on the display screen. According to an example embodiment, a first border line 705a may be provided at an outer boundary of the iris of the eye. According to an example embodiment, a second border line 705b may be provided at an inner boundary of the iris of the eye. According to an example embodiment, the first border line 705a and the second border line 705b may be simultaneously provided as a double border. According to another example embodiment, the first border line 705a and the second border line 705b may be independently or separately displayed. According to another example embodiment, the first border line 705a and the second border line 705b may be depicted by circular and dashed boundary lines. However, the boundary lines are not limited to the dashed lines, and thus other manners of depicting the boundary may be provided according to other example embodiments.

According to an example embodiment in FIG. 7A, an eye selection function may be provided that allows a user to select between a right eye image and a left eye image of the subject. For instance, when icon 709 is selected, a right eye image may be displayed in the region 701 and when selection icon 710 is selected, a left eye image may be displayed in the region 701. Similar icons 709 and 710 may be separately provided corresponding to region 702. According to another example embodiment, one icon 709 and one icon 710 may be provided for both the regions 701 and 702. According to another example embodiment, the icons 709 and 710 may be a thumbnail or smaller version of the right eye image or the left eye image.

Figure 7B:
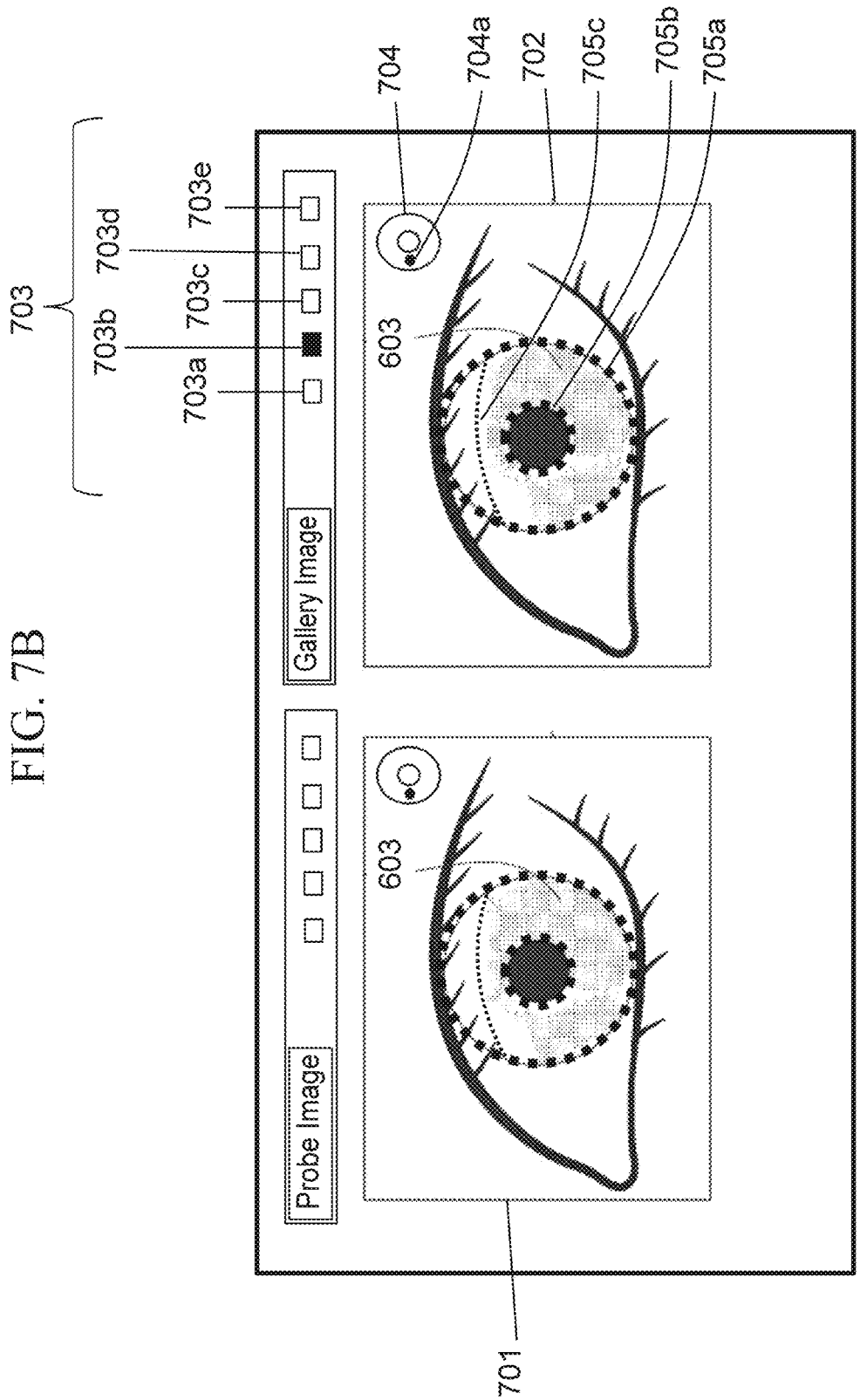

According to an example embodiment in FIG. 7B, a border function may be provided that draws a boundary between the iris of the eye and the eyelashes. For instance, when icon 703b is selected, the processor 101 identifies a boundary between the iris and the eyelashes and generates a border to be provided on the displayed eye image on the display screen. According to an example embodiment, a third border line 705c may be provided at an outer boundary of the iris of the eye.

According to an example embodiment, the first border line 705a, the second border line 705b and the third border line 705c may be simultaneously displayed. According to another example embodiment, the first border line 705a, the second border line 705b and the third border line 705c may be independently or separately displayed. According to another example embodiment, the third border line 705c may be depicted by partially circular and dashed boundary lines. However, the boundary line is not limited to the partially circular or dashed lines, and thus other manner of depicting the boundary may be provided according to other example embodiments.

With the use of the boundary lines 705a, 705b and 705c, the user is able to easily identify and/or focus on a region or regions of interest in the eye. Furthermore, the user can align, verify and confirm the result of the comparison between two images in a more comprehensible manner.

Figure 7C:
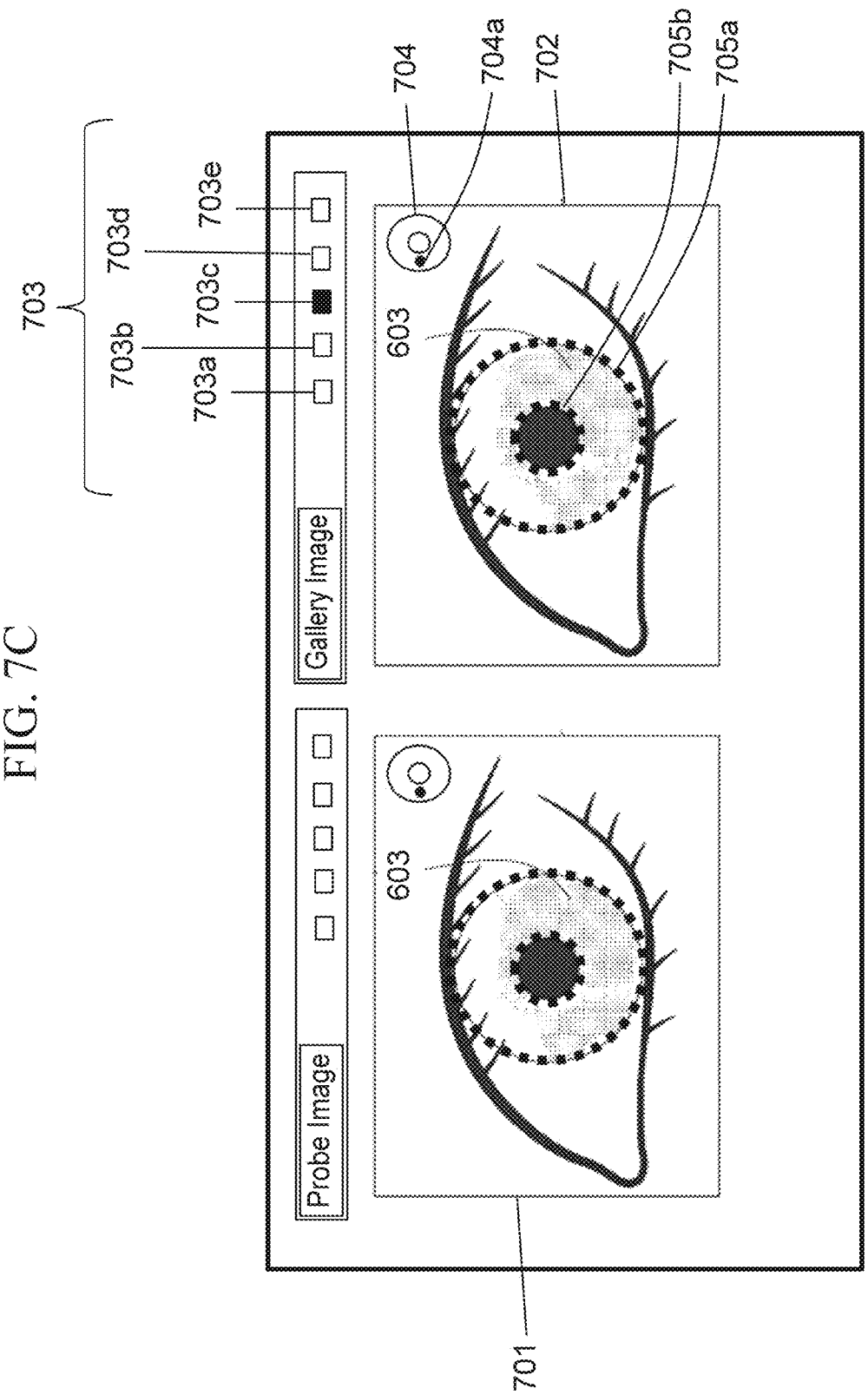

According to another example embodiment illustrated in FIG. 7C, a rotate function is provided that allows a user to rotate the image of the eye. For example, when icon 703c is selected, the display screen 700 displays a dial 704 having a pointer 704a representing a position of rotation of the iris. For example, as the user rotates the iris image around a central axis of the pupil of the eye, the pointer 704a moves around the dial in a corresponding manner. According to an example embodiment, one or more pieces of information 603 may be provided on the iris region of the eye image. According to another example embodiment, the user rotates the iris image without the one or more pieces of information 603 provided on the iris region of the eye. In this manner, the user is able to easily align images of the eye. Furthermore, the user can verify and confirm the result of the comparison in a more comprehensible manner.

According to an example embodiment, the one or more pieces of information may be feature amounts calculated in operation S105 in FIG. 4. According to another example embodiment, the one or more pieces of information may be an iris code of the eye.

Figure 7D:
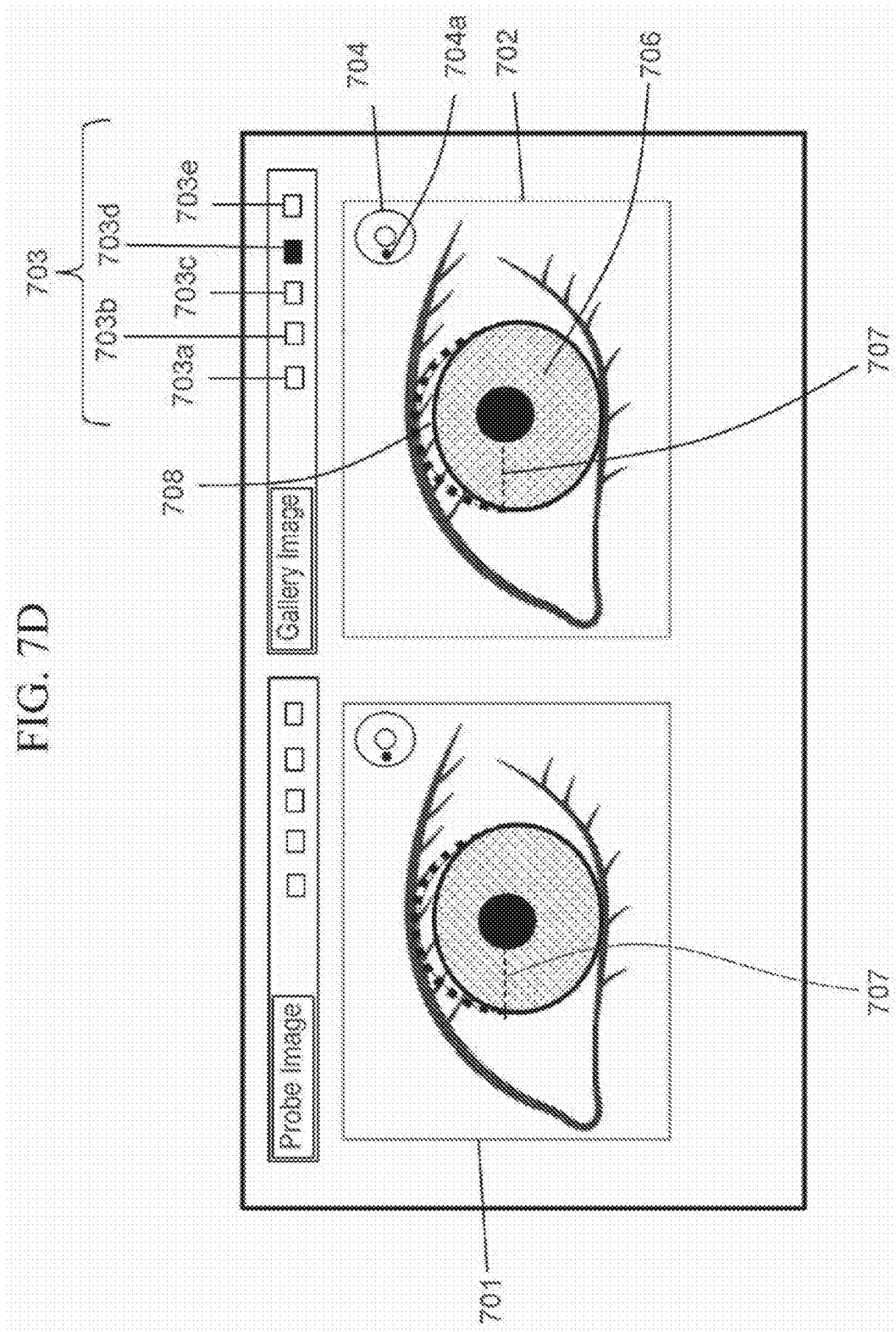

According to an example embodiment in FIG. 7D, a highlighting function may be provided that highlights the iris region of the eye. For instance, when icon 703d is selected, the processor 101 identifies the iris region and highlights 706 the iris region. According to an example embodiment, the processor highlights the iris region by coloring the iris region with a predetermined color. According to another example embodiment, the processor 101 may highlight the iris region by shading the iris region. According to yet another example embodiment, the processor 101 may highlight the iris region by providing other types of markings to highlight the iris region.

According to an example embodiment, the processor 101 may not highlight a portion of the iris region 708 that is overlapped by the eyelashes. According to another example embodiment, an alignment marker 707 may be provided to indicate the position of the iris region. For example, as the user rotates the dial 704, the alignment marker 707 may rotate to convey to the user the rotated position of the iris. By highlighting the region of focus and/or by providing an alignment marker, the user is able to easily identify and/or focus on a region or regions of interest in the eye. Furthermore, the user can align, verify and confirm the result of the comparison between two images in a more comprehensible manner.

One or more functions illustrated in FIGS. 7A-7E above, and other functions may be performed alone or in combination with one another according to other example embodiments of the disclosure.

According to another example embodiment, one or more functions illustrated in FIGS. 7A-7E above, and other functions may be performed for a single eye, instead of a comparison between two eyes. In this manner, the user may able to focus on a region of interest even in a single eye with or without performing a comparison. For instance, the may be able to identify and verify a quality of the captured eye image before storing in a gallery for future authentication or comparison.

Figure 8:
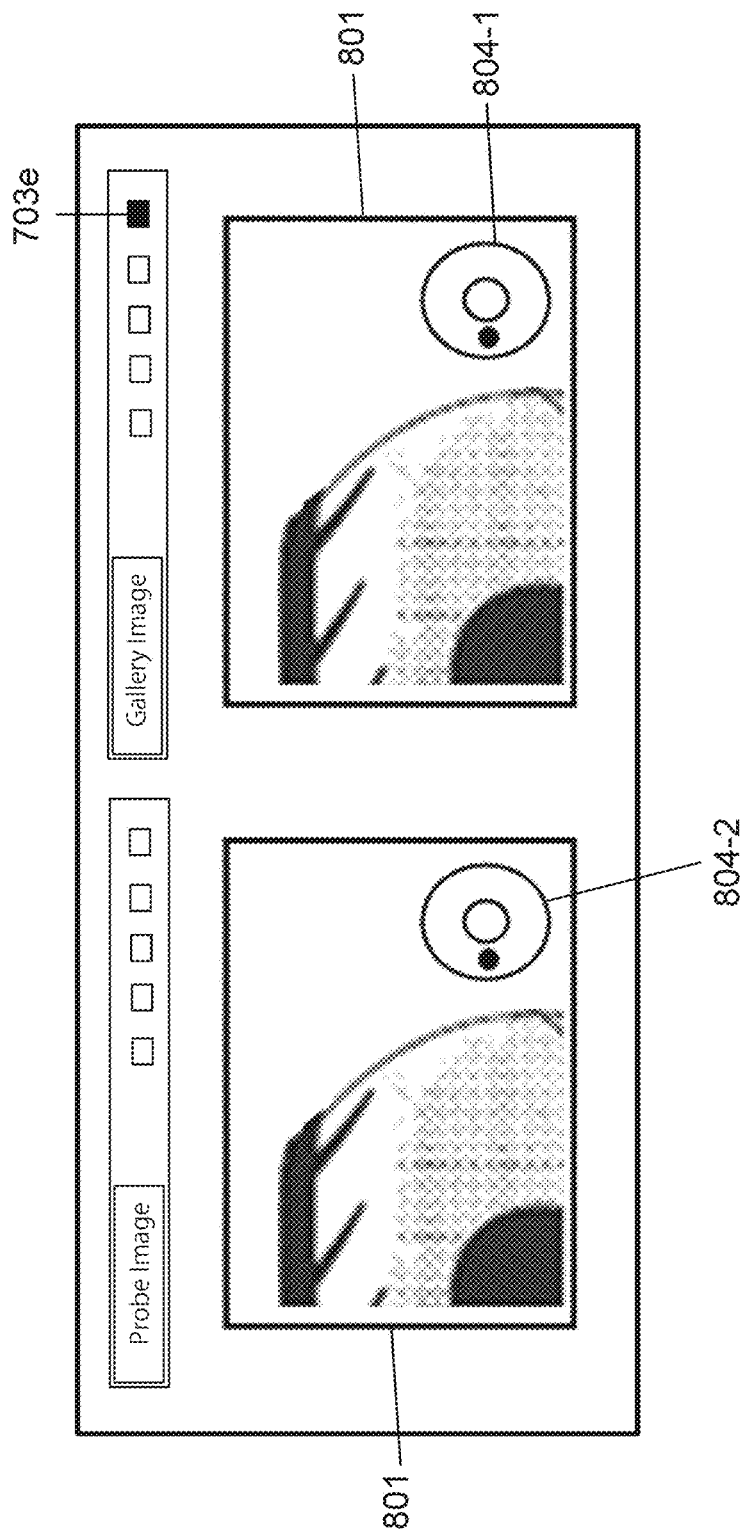
FIG. 8 illustrates an example of a display screen displayed by the information processing system according to another example embodiment.

FIG. 8 is a display example of the display regions 801 and 802 when iris images are focused. According to an example embodiment, the iris image may be focused based on a user performing a zoom operation by selecting icon 703e. When the inside parts of circles surrounded by dotted lines in FIG.

6 are focused on, the user can see the patterns of the feature amounts indicated in the display regions 801 and 802 in more detail. For instance, as illustrated in an example embodiment in FIG. 8, a quarter region of the iris image is displayed with a center of the pupil being a center rotation in display regions 801 and 802. As such, the user is able to rotate the iris image in one or both of the display regions 801 and 802 to more easily align the images and/or verify a result of the comparison.

According to an example embodiment, the iris image in display region 801 and the iris image in display region 802 may be simultaneously controlled by one of dials 804-1 and 804-2. According to another embodiment, the iris image in display region 801 and the iris image in display region 802 may be independently controlled by separate dials 804-1 and 804-2. According to another example embodiment, a single dial 704 may be provided instead of two dials illustrated in FIG. 8, and when the user rotates the single of the dial, both the iris images respectively displayed in the in display regions 801 and 802 may simultaneously rotate.

In such a way, the information processing system 10 can display a feature amount image in association with positions in an iris of a recognition subject. Thus, the user of the information processing system 10 may know not only information on a comparison result, but also specific information as to which position and what degree the feature amount is matched. Thereby, the user may further know information regarding a matching region, a non-matching region, or a non-comparable region of the feature amount for each position in an iris.

Some of the advantages in the user of the information processing system 10 obtaining the above information will be described. As described above, when feature amounts are extracted from an iris image, the shape is often transformed for the purpose of increasing efficiency of processing or the like. In such a case, even if the obtained feature amounts are displayed, the correspondence between the feature amounts and positions in the iris may be unknown, and thus such display may not so useful for the user. In contrast, since the information processing system 10 of the example embodiment transforms a feature amount image into a ring shape and then displays the transformed image in association with positions in an iris of a recognition subject, the user may clearly understand the correspondence between the feature amounts and the positions in the iris.

Moreover, a case where it is desirable for the user to understand the correspondence between feature amounts and positions in an iris will be described with some examples. When eyelashes, a hair, an eyelid, or the like of a recognition subject overlaps an iris, accurate comparison results may not be obtained. In those situations, it is not always easy to identify the reason why an accurate comparison result was unable to be obtained from only the comparison result. When eyelashes, a hair, an eyelid, or the like overlaps an iris, typically, non-matching regions or non-comparable regions concentrate in the upper side in an iris. In such a way, when accurate comparison result cannot be obtained, a feature may often appear at a position in the non-matching region or the non-comparable region. Accordingly, by identifying a location of a non-matching region or a non-comparable region by rotating the image of the iris, the user can determine whether or not a comparison result is correct.

According to another example, identity verification automatically performed by an iris recognition apparatus may not always reliable. Accordingly, in a situation where it is necessary to carefully perform identity verification, a human may finally review the comparison detail such as a matching part or the like in addition to an automatic comparison performed by the information processing system 10. Thus, a function of visually reviewing a feature amount may be desired. In such a case, even if feature amounts in rectangles used for comparison are displayed, it is not easy for a human viewing this display to identify which location of an iris the patterns are matched and perform the final confirmation of the comparison detail. However, since the information processing system 10 of the example embodiment transforms a feature amount image into a ring shape fitted to the shape of an iris, and further allows the user to rotate the iris image added with the feature amount, it is possible to easily identify which location in the iris the pattern is matched, which location in the iris the pattern is unmatched, and/or which location in the iris the pattern in non-comparable. For instance, the user may rotate one or both of the "Probe Image" and the "Gallery Image" in FIGS. 7A-7D and 8 into alignment with each other to easily identify whether there is a matched location in the iris the pattern between the two images.

As described above, according to the example embodiments, it is possible to provide an information processing system, an information processing method, and an information processing program that can display information regarding iris comparison in more detail.

Note that the method of generating a display image of the example embodiment may be used regardless of a method of extracting a feature amount or regardless of the one or more pieces of information that may be superimposed on the image of the iris.

As described in the illustration of Portion (i) of FIG. 3 and operation S108 in FIG. 4, although it is possible to allow the user to easily know the positional correspondence between feature amounts and an iris by superimposing feature amounts on an image of an eye, this disclosure is not limited thereto. For example, the configuration of the example embodiment may be modified so that a feature amount image transformed into a ring shape as illustrated in Portion (h) of FIG. 3 is displayed on the display unit 128 without being superimposed on an image of an eye. In such a case, a process can be simplified.

According to another example, instead of displaying the entirety of the feature amounts of the iris image, only the matching regions and/or the non-matching regions of the feature amount may be displayed on the display regions 701, 702, 801 and 802. Accordingly, in another example embodiment, only representations of the feature amounts, the matching regions or the non-matching regions may be displayed. According to another example embodiment, the display of the matching region and the non-matching region may be displayed by being colored with different colors to highlight potential regions for the user to focus. According to other example embodiments, the potential regions may be highlighted by shading, marking, brightening/darkening or user other methods.

Figure 10:
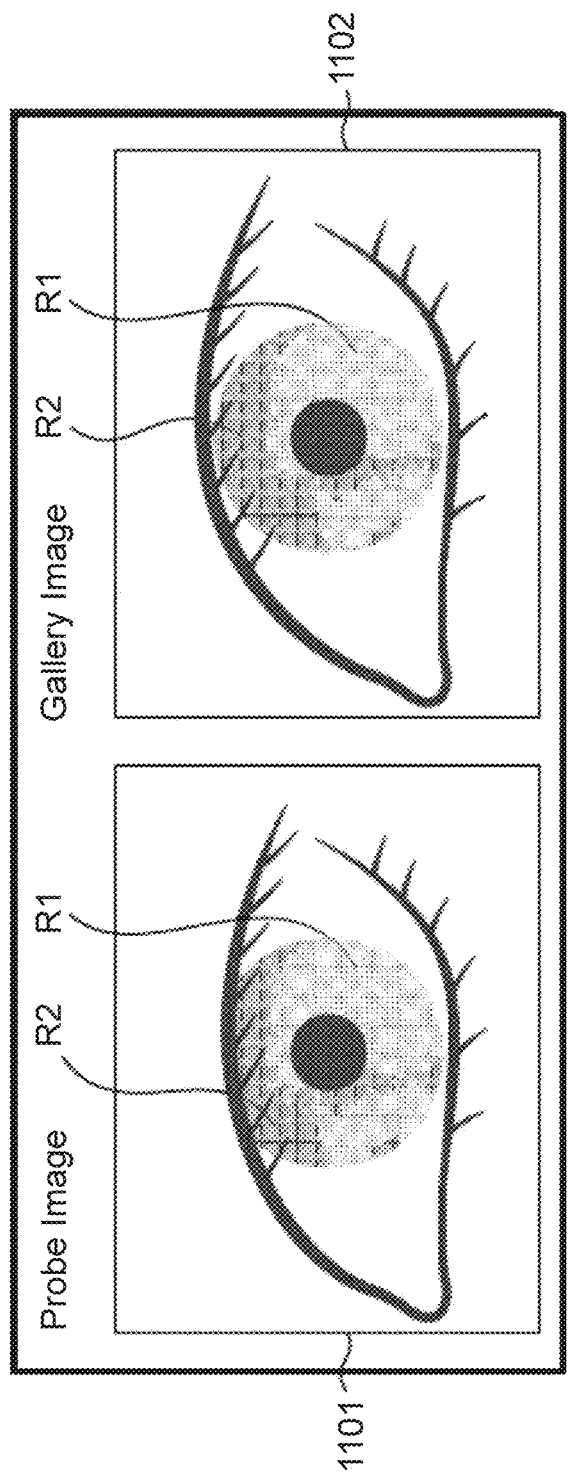
FIG. 10 illustrates an example of a display image when iris images of are compared.

According to another example embodiment, a matching region, a non-matching region and/or a non-comparable region may be displayed on the display regions. FIG. 10 illustrates an example of a display image when iris images of are compared. According to FIG. 10, a matching region R1 and a non-matching region R2 may be provided in a display region 1101 corresponding to a probe image and a matching region R1 and a non-matching region R2 may be provided in a display region 1102 corresponding to a gallery image according to an example embodiment.

According to another example embodiment, a non-comparable region may be further displayed to distinguish from the matching region R1 and the non-matching region R2. In such a case, the matching region R1, the non-matching region R2, and the non-comparable region may be displayed by being colored in different colors. This enables the user to further obtain information on the non-comparable region. Alternatively, any two of the matching region R1, the non-matching region R2, and the non-comparable region may have the same color. Also in this case, one region and the remaining regions can be distinguished and displayed.

According to another example embodiment, the above described display regions 701, 702, 801 and 802 may display the image of the eye without superimposing one or more pieces of information corresponding to an image of an eye. In this manner, the user may be able to rotate and align the images of the eye even without the feature amounts from operation S106.

Figure 9:
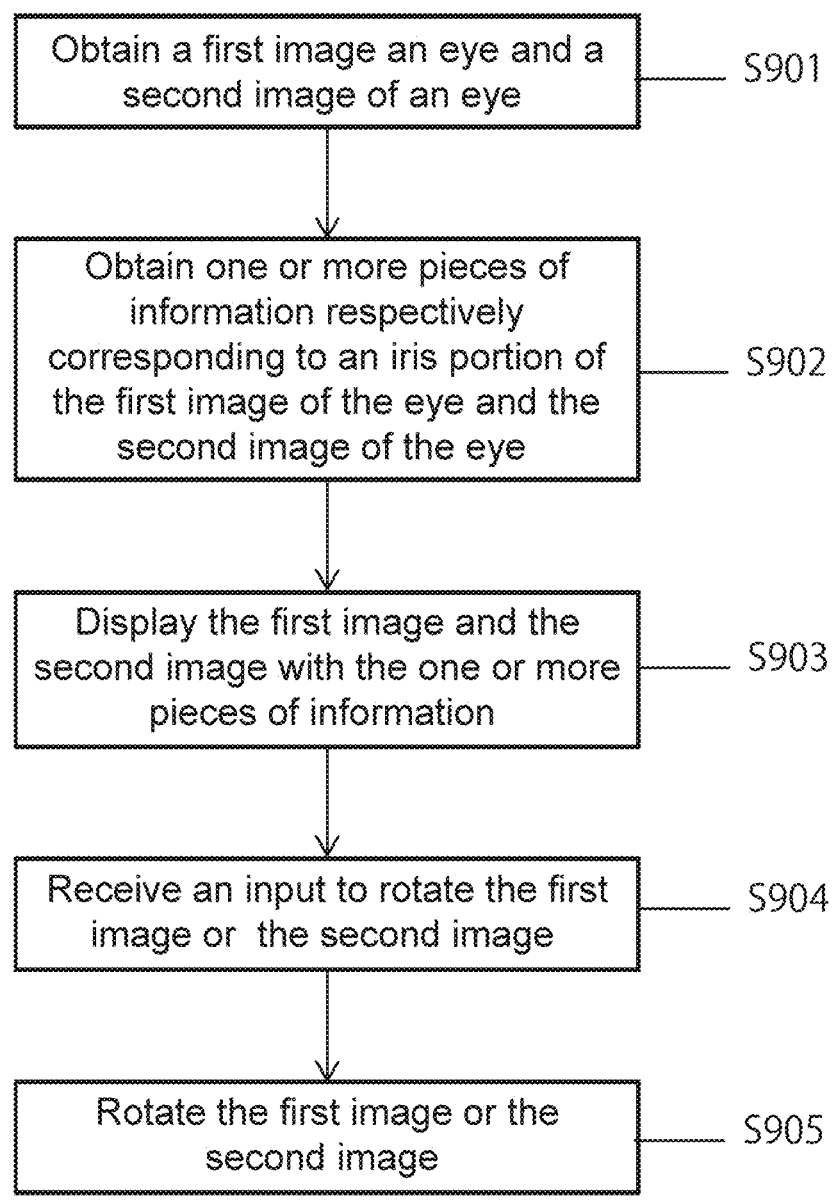
FIG. 9 is a flowchart illustrating the outline of a process for generating the display screen according to the example embodiment.

FIG. 9 is a flowchart illustrating the outline of the process performed by the information processing system 10 for generating a graphical user interface in FIGS. 7 and 8 according to an example embodiment. With reference to FIGS. 3, 7 and 8, if necessary, the outline of the process performed by the information processing system 10 will be described along the flowchart of FIG. 9.

In S901, the processor 101 acquires a first image an eye and a second image of an eye. According to an example embodiment, the first image of the eye may be an image of a recognition subject, and the first image may be a candidate for comparison with the second image of an eye. According to an example embodiment, the second image of the eye may be an image obtained from a storage storing a plurality of preregistered images each corresponding to one of a plurality of eyes.

In S902, the processor 101 obtains one or more pieces of information respectively corresponding to an iris portion of the first image of the eye and the second image of the eye. According to an example embodiment, the one or more pieces of information may be feature amount calculated in operation S105 in FIG. 4, iris code of the eye, representations of a result of a comparison in operation S105 (such as an indication of a matching region, an indication of a non-matching region or an indication of a region unable to be compared).

In S903, the processor 101 controls the display unit 128 (in FIG. 1) to display the first image and the second image by adding the respective one or more pieces of information thereon. According to an example embodiment, the processor 101 may display the first image and the second image without adding the one or more pieces of information.

In S904, the processor 10 receives an input from an input device 107 (in FIG. 1) to rotate the first image, the second image, or both the first and the second image.

In S905, the processor 101 rotates the first image, the second image or both the first image and the second image based on the input and controls the display unit 128 to display the first image or the second image in a rotated state based on the input. According to an example embodiment, the processor 101 rotates the iris image around a central axis of the pupil of the eye. In this manner, the user is able to easily align the iris portion in the first image and iris portion in the second image to view the iris portions in detail. In this manner, the user may be able to more easily verify the result of the comparison.

According to the example embodiment, it is possible to provide an information processing system that can display information regarding iris comparison in more detail to allow a user to verify the reliability of the iris comparison.

The disclosure is not limited to the example embodiments described above but can be changed as appropriate within a range not departing from the spirit of the disclosure.

In one or more of the example embodiments described above, acquisition of an image used in iris comparison may be performed on one of the eyes or may be performed on both of the eyes of an authentication subject. Advantages of improvement of a processing speed and reduction in a storage capacity are obtained when an image of one of the eyes is captured, and an advantage of improvement of authentication accuracy is obtained when images of both of the eyes are acquired.

While the information processing devices and systems used in iris comparison have been illustrated as examples in each of the above example embodiments, the disclosure is also applicable to biometrics recognition other than iris comparison by appropriately changing the configuration of the one or more example embodiments. For example, the disclosure is also applicable to vein recognition in which the pattern of a vein of a palm, a finger, or the like is recognized to perform identity verification. In the case of vein recognition of a palm, the same display as that in the case of iris comparison can be performed by the content of comparison information being superimposed on an image of a palm and displayed.

The scope of one or more example embodiments also includes a processing method of storing, in a storage medium, a program that causes the configuration of the example embodiment to operate to implement the function of the example embodiment described above, reading out as a code the program stored in the storage medium, and executing the code in a computer. That is, a computer readable storage medium is also included in the scope of each example embodiment. Further, not only the storage medium in which the program described above is stored but also the program itself is included in each example embodiment. Further, one or more components included in the example embodiments described above may be a circuit such as an Application Specific Integrated Circuit (ASIC), a Field Programmable Gate Array (FPGA), or the like configured to implement the function of each component.

As the storage medium, for example, a floppy (registered trademark) disk, a hard disk, an optical disk, a magneto-optical disk, a Compact Disk (CD)-ROM, a magnetic tape, a nonvolatile memory card, or a ROM can be used. Further, the scope of each of the example embodiments includes an example that operates on Operating System (OS) to perform a process in cooperation with another software or a function of an add-in board without being limited to an example that performs a process by an individual program stored in the storage medium.

The service implemented by the function of one or more example embodiments described above can be provided to the user in a form of Software as a Service (SaaS).

Note that all the example embodiments described above are mere examples of embodiment in implementing the disclosure, and the technical scope of the disclosure should not be construed in a limiting sense by these example embodiments. That is, the disclose can be implemented in various forms without departing from the technical concept thereof or the primary feature thereof.

The example embodiments described above may also be described entirely or in part by the following supplementary notes, without being limited to the following.

(Supplementary Note 1)

An information processing apparatus comprising:

a memory configured to store one or more instructions; and a processor configured to execute the one or more instructions to:

obtain a first image including a first representation of an iris region of a first eye;

obtain a second image including a second representation of an iris region of a second eye;

receive an input to rotate at least one of the first image or the second image; and control a display to display the at least one of the first image or the second image in a rotated state based on the input.

(Supplementary Note 2)

The information processing apparatus of supplementary note 1, wherein the first representation is based on a first feature amount calculated for the iris region of the first eye in the first image, and wherein the second representation is based on a second feature amount calculated for the iris region of the second eye in the second image.

(Supplementary Note 3)

The information processing apparatus of supplementary note 1, wherein the first representation and the second representation are based on a result of comparison between the iris region of the first eye in the first image and the iris region of the second eye in the second image.

(Supplementary Note 4)

The information processing apparatus of supplementary note 3, wherein the first representation and the second representation comprise an indication of a matching region, a non-matching region, or a non-comparable region based on the results of the comparison.

(Supplementary Note 5)

The information processing apparatus of supplementary note 4, wherein the matching region, the non-matching region, or the non-comparable region is indicated by coloring the iris region of the first eye in the first image or the iris region of the second eye in the second image in in a predetermined color.

(Supplementary Note 6)

The information processing apparatus of supplementary note 2, wherein the processor is further configured to generate the first feature amount and the second feature amount by dividing the iris region of the first eye in the first image and the iris region of the second eye in the second image into a plurality of blocks associated with the positions in the iris of the respective eye, and setting a code extracted from the iris image for each of the plurality of blocks.

(Supplementary Note 7)

The information processing apparatus of supplementary note 1, wherein the first representation is based on a coded image corresponding to the iris region of the first eye in the first image, and wherein the second representation is based on coded image corresponding to the iris region of the second eye in the second image.

(Supplementary Note 8)

The information processing apparatus of supplementary note 1, wherein the processor is further configured to simultaneously display the first image and the second image.

(Supplementary Note 9)

The information processing apparatus of supplementary note 1, wherein the processor is further configured to display a dial icon for guiding a user to input an instruction to rotate the first image and the second image.

(Supplementary Note 10)

The information processing apparatus of supplementary note 1, wherein the processor is further configured to display a dial icon for guiding a user to input an instruction to align the first image with the second image.

(Supplementary Note 11)

The information processing apparatus of supplementary note 1, wherein the first image is a photograph of an eye of a recognition subject, and wherein the second image is a registered image, among a plurality of registered images stored in a storage.

(Supplementary Note 12)

The information processing apparatus of supplementary note 1, wherein the representation comprises a boundary line depicting the boundary of the iris region of the eye in the image.

(Supplementary Note 13)

The information processing apparatus of supplementary note 12, wherein the boundary line includes a boundary portion between the iris region and the eyebrow.

(Supplementary Note 14)

The information processing apparatus of supplementary note 1, wherein the representation comprises a highlighted region depicting the iris region of the eye in the image.

(Supplementary Note 15)

The information processing apparatus of supplementary note 14, wherein the highlighted region includes a predetermined color.

(Supplementary Note 16)

An information processing method comprising:

obtaining a first image including a first representation of an iris region of a first eye;

obtaining a second image including a second representation of an iris region of a second eye;

receiving an input to rotate at least one of the first image or the second image; and controlling a display to display the at least one of the first image or the second image in a rotated state based on the input.

(Supplementary Note 17)

The information processing method of supplementary note 16, wherein the first representation is based on a first feature amount calculated for the iris region of the first eye in the first image, and wherein the second representation is based on a second feature amount calculated for the iris region of the second eye in the second image.

(Supplementary Note 18)

The information processing method of supplementary note 16, wherein the first representation and the second representation are based on a result of comparison between the iris region of the first eye in the first image and the iris region of the second eye in the second image.

(Supplementary Note 19)

The information processing method of supplementary note 18, wherein the first representation and the second representation comprise an indication of a matching region, a non-matching region, or a non-comparable region based on the results of the comparison.

(Supplementary Note 20)

The information processing method of supplementary note 19, wherein the matching region, the non-matching region, or the non-comparable region is indicated by coloring the iris region of the first eye in the first image or the iris region of the second eye in the second image in a predetermined color.

(Supplementary Note 21)

The information processing method of supplementary note 17, further comprising:
generating the first feature amount and the second feature amount by dividing the iris region of the first eye in the first image and the iris region of the second eye in the second image into a plurality of blocks associated with the positions in the iris of the respective eye, and setting a code extracted from the iris image for each of the plurality of blocks.

(Supplementary Note 22)

The information processing method of supplementary note 16, wherein the first representation is based on a coded image corresponding to the iris region of the first eye in the first image, and
wherein the second representation is based on coded image corresponding to the iris region of the first eye in the second image.

(Supplementary Note 23)

The information processing method of supplementary note 15, further comprising:
displaying a dial icon for guiding a user to input an instruction to rotate the first image and the second image.

(Supplementary Note 24)

A non-transitory computer readable medium having stored thereon a program for performing a method comprising:
obtaining a first image including a first representation of an iris region of a first eye;
obtaining a second image including a second representation of an iris region of a second eye;
receiving an input to rotate at least one of the first image or the second image; and
controlling a display to display the at least one of the first image or the second image in a rotated state based on the input.

(Supplementary Note 25)

An information processing apparatus comprising:
a memory configured to store one or more instructions; and
a processor configured to execute the one or more instructions to:
obtain an image including a representation of an iris region of an eye;
receive an input to rotate the image; and
control a display to display the image in a rotated state based on the input.

(Supplementary Note 26)

The information processing apparatus of supplementary note 25, wherein the representation is based on a feature amount calculated for the iris region of the eye in the image.

(Supplementary Note 27)

The information processing apparatus of supplementary note 26, wherein a visual representation of feature amount is overlaid on the iris region of the eye in the image.

(Supplementary Note 28)

The information processing apparatus of supplementary note 25, wherein the representation comprises a boundary line depicting the boundary of the iris region of the eye in the image.

(Supplementary Note 29)

The information processing apparatus of supplementary note 28, wherein the boundary line includes a boundary portion between the iris region and the eyelashes.

(Supplementary Note 30)

The information processing apparatus of supplementary note 25, wherein the representation comprises a highlighted region depicting the iris region of the eye in the image.

(Supplementary Note 31)

The information processing apparatus of supplementary note 30, wherein the highlighted region includes a predetermined color.

This application is based upon and claims the benefit of priority from U.S. provisional patent application No. 62/884,833, filed Aug. 9, 2019, the disclosure of which is incorporated herein in its entirety.

The invention claimed is:

1. An information processing apparatus comprising:
a memory configured to store one or more instructions; and
a processor configured to execute the one or more instructions to:
obtain a first image including a first representation of an iris region of a first eye;
obtain a second image including a second representation of an iris region of a second eye;
identify a boundary between eyelashes and the iris region in at least one of the first image or the second image;
control a display to display the at least one of the first image or the second image in a rotated state; and
superimpose the boundary in at least one of the first image or the second image.

2. The information processing apparatus of claim 1, wherein the first representation is based on a first feature amount calculated for the iris region of the first eye in the first image, and
wherein the second representation is based on a second feature amount calculated for the iris region of the second eye in the second image.

3. The information processing apparatus of claim 2, wherein the processor is further configured to generate the first feature amount and the second feature amount by dividing the iris region of the first eye in the first image and the iris region of the second eye in the second image into a plurality of blocks associated with the positions in the iris of the respective eye, and setting a code extracted from the iris image for each of the plurality of blocks.

4. The information processing apparatus of claim 1, wherein the first representation and the second representation are based on a result of comparison between the iris region of the first eye in the first image and the iris region of the second eye in the second image.

5. The information processing apparatus of claim 4, wherein the first representation and the second representation comprise an indication of a matching region, a non-matching region, or a non-comparable region based on the results of the comparison.

6. The information processing apparatus of claim 5, wherein the matching region, the non-matching region, or the non-comparable region is indicated by coloring the iris region of the first eye in the first image or the iris region of the second eye in the second image in a predetermined color.

7. The information processing apparatus of claim 1, wherein the first representation is based on a coded image corresponding to the iris region of the first eye in the first image, and wherein the second representation is based on a coded image corresponding to the iris region of the second eye in the second image.

8. The information processing apparatus of claim 1, wherein the processor is further configured to simultaneously display the first image and the second image.

9. The information processing apparatus of claim 1, wherein the first image is a photograph of an eye of a recognition subject, and wherein the second image is a registered image, among a plurality of registered images stored in a storage.

10. The information processing apparatus of claim 1, wherein the first representation comprises a boundary line depicting the boundary of the iris region of the first eye in the first image.

11. The information processing apparatus of claim 10, wherein the boundary line includes a boundary portion between the iris region and an eyebrow.

12. An information processing method comprising:
    obtaining a first image including a first representation of an iris region of a first eye;
    obtaining a second image including a second representation of an iris region of a second eye;
    identifying a boundary between eyelashes and the iris region in at least one of the first image or the second image;
    controlling a display to display the at least one of the first image or the second image in a rotated state; and
    superimposing the boundary in at least one of the first image or the second image.

13. The information processing method of claim 12, wherein the first representation is based on a first feature amount calculated for the iris region of the first eye in the first image, and
    wherein the second representation is based on a second feature amount calculated for the iris region of the second eye in the second image.

14. The information processing method of claim 12, wherein the first representation and the second representation are based on a result of comparison between the iris region of the first eye in the first image and the iris region of the second eye in the second image.

15. The information processing method of claim 14, wherein the first representation and the second representation comprise an indication of a matching region, a non-matching region, or a non-comparable region based on the results of the comparison.

\* \* \* \* \*